United States Patent [19]

Skorianetz

[11] B 3,981,892
[45] Sept. 21, 1976

[54] POLYCYCLIC LACTONES AS ODOR- AND TASTE-MODIFYING AGENTS

[75] Inventor: Werner Skorianetz, Geneva, Switzerland

[73] Assignee: Firmenich S.A., Geneva, Switzerland

[22] Filed: July 23, 1974

[21] Appl. No.: 491,032

[44] Published under the second Trial Voluntary Protest Program on February 10, 1976 as document No. B 491,032.

[30] Foreign Application Priority Data

Aug. 1, 1973 Switzerland.................... 11267/73

[52] U.S. Cl.......................... 260/343.2 R; 252/522; 426/536
[51] Int. Cl.$^2$........................................ C07D 493/00
[58] Field of Search ............................ 260/343.2 R

[56] References Cited
OTHER PUBLICATIONS

House Modern Synthetic Reactions, 2nd Ed. (1972), pp. 321–327.

Primary Examiner—James A. Patten
Attorney, Agent, or Firm—Pennie & Edmonds

[57] ABSTRACT

New polycyclic lactones useful as perfuming and odor-modifying agents in the manufacture of perfumes and perfumed articles, and as flavoring and taste-modifying agents in the aromatization of foodstuffs in general and imitation flavors for foodstuffs, beverages, animal feeds, pharmaceutical preparations and tobacco products.

Novel process for the preparation of said cycloaliphatic compounds and compositions of matter relating to mixtures containing same.

4 Claims, No Drawings

POLYCYCLIC LACTONES AS ODOUR- AND TASTE-MODIFYING AGENTS

SUMMARY OF THE INVENTION

The compounds to which the present invention relates belong to the class of tricyclic derivatives having the formula

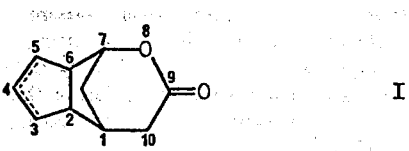

wherein one of the rings contains a single or a double bond in one of the positions indicated by the dotted lines.

The following are specific examples of compounds of formula I:

8-oxatricyclo[5.3.1.0$^{2,6}$]undecan-9-one,
8-oxatricyclo[5.3.1.0$^{2,6}$]undec-3-en-9-one, and
8-oxatricyclo[5.3.1.0$^{2,6}$]undec-4-en-9-one.

The compounds of the invention possess interesting organoleptic properties and, accordingly, are useful as perfuming and odour-modifying agents, and as flavouring and taste-modifying agents.

The present invention relates also to a process for the preparation of the compounds of formula I, which process comprises reacting a tricyclic ketone of formula

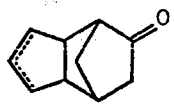

wherein one of the rings contains a single or a double bond in one of the positions indicated by the dotted lines, with an organic peracid.

BACKGROUND OF THE INVENTION

In the course of the last decade particularly, an increasing attention is being devoted to the preparation and utilization of artificial perfuming- and odour-modifying agents possessing the skeleton of tricyclo[5.2.1.0.$^{2,6}$]decane. This attention has certainly been stimulated mainly by an increased availability of the compounds acting as starting materials in the aforementioned preparations.

It has been shown for instance (see German Pat. No. 1,617,021) that the compounds of formula

wherein R represents an acyl group or a hydrogen atom, possess a perfuming note reminiscent of that developed by lavender oil. According to laid open to public inspection Dutch Patent Application No. 6901750, the polycyclic γ,δ-unsaturated aldehyde of formula

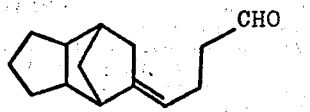

develops a green-fruity character which is reminiscent of the lily-of-the-valley fragrance.

3a,4,7,7a-Tetrahydro-4,7-methanoindene and 2,3,3a,4,7,7a-hexahydro-4,7-methanoindene have been also described as compounds possessing an interesting marked woody character (see: U.S. Pat. No. 3,542,877).

We have now surprisingly found that the compounds of formula I possess interesting organoleptic properties and, accordingly, are useful ingredients in the perfumery and in the flavour industry.

PREFERRED EMBODIMENTS OF THE INVENTION

The compounds of the invention can be compounded with other odoriferous substances, to make perfume compositions, in a manner conventional in the perfumery art; they can be used, combined with carriers or diluents, for perfuming a wide range of products; they can be used to modify, enhance or improve the organoleptic properties of foodstuffs, animal feeds, beverages, pharmaceutical preparations and tobacco products; and they can also be used in the manufacture of artificial flavouring compositions.

The term "foodstuff" is used here broadly, and includes coffee, tea and chocolate.

The compounds of the invention develops fatty, fruity and spicy notes reminiscent, particularly with regard to their sweetish character, to certain fragrance nuances typical of coumarin.

In the perfumery the compounds of the invention are particularly suited to the reconstitution of various floral essential oils.

Moreover, it has been found that the compounds of formula I help to balance or harmonize the odoriferous effect of certain perfuming compositions, mainly by improving their top notes.

When used as perfuming agents, the compounds of formula I can typically be used at concentration of between about 0.5 and 10 % by weight of the total weight of the compositions to which they are added. These proportions can be increased in special cases, typically for the preparation of certain reconstituted essential oils wherein compounds I can constitute up to 70 or even 80 % of the total weight of the composition, and the amount can be smaller in perfumed products such as soaps or detergents. When used as flavouring agents, the compounds of formula I can develop gustative notes which present a great analogy with those presented by coumarin itself, and, accordingly, compounds I, in certain cases, can be used in combination with other flavouring ingredients for conferring to foodstuffs a coumarinic flavour note.

These flavouring characters are particularly suitable for the aromatization of syrups, jams, milk, yoghourts, puddings, ice-creams, and bakery or confectionary products. The compounds of the invention can equally find a useful application in the aromatization of tobacco and tobacco products wherein the spicy and fruity note is particularly appreciated.

Interesting flavouring effects can typically be achieved with proportions ranging from 10 to 100 ppm of the compounds of the invention, based on the weight of the product flavoured; but amounts higher than those indicated can be used for special effects. When the compounds of formula I are used in flavouring compositions, in admixtures with other flavouring agents, they may typically constitute from 5 to 20 % of the total weight of such compositions.

In accordance with the present invention, compounds I are prepared according to a process which comprises reacting tricyclic ketone II with an organic peracid.

Known techniques can be used for carrying out this process which proceeds in accordance with the Bayer-villiger type reaction (cf. e.g. H. O. House, Modern Synthetic Reactions, W. A. Benjamin, Inc., New York (1965), p. 123 and ff.). Thus, for example, the mentioned reaction can suitably be performed by the action of a peracid such as performic, peracetic, trifluoroperacetic, monopermaleic, perbenzoic or monoperphthalic acid; peracetic acid is preferred. The organic peracids can be generated in situ by the action of hydrogen peroxide on the corresponding organic acid. The reaction can be effected in an aqueous medium in the presence of an inert organic solvent such as, e.g., a halogenated hydrocarbon, e.g. dichloromethane, dichloroethane, chloroforme, trichloroethylene or dichloroethylene.

According to a preferred embodiment of the present invention, the conversion of ketone II into its corresponding lactone I is performed in a buffered medium. Typical buffer agents are alkali metal salts of organic acids. Thus, sodium or potassium formate, acetate, propionate, butyrate, oxalate, citrate or tartrate can be conveniently used. Sodium acetate, in an aqueous organic medium comprising dichloromethane, is preferred.

The temperature at which the reaction is carried out will depend upon a variety of factors, including the reaction rate, the particular reactants used and the solvents employed. Generally, however, the reaction is effected at room temperature or at a temperature lying in the vicinity of room temperature. In order to achieve the best yields in the final product, the solution containing the organic peracid is added at a certain rate to the cooled mixture comprising ketone II until said mixture reaches the preselected temperature which is then kept stable by external cooling.

The invention is better illustrated by the following Examples wherein the temperatures are indicated in degrees centigrade and the abbreviations have the meaning common in the art.

EXAMPLE 1

8-Oxatricyclo[5.3.1.0$^{2,6}$]undecan-9-on 18 g of a 50 % peracetic acid solution in acetic acid containing 1 g of sodium acetate were added to a stirred mixture of 15 g of tricyclo[5.2.1.0$^{2,6}$]decane-8-one (which can be purchased from Ruhrchemie, Bruchstrasse, D-42 Oberhausen Holten, West Germany) and 9 g of anhydrous sodium acetate in 60 g of dichloromethane. The temperature of the reaction mixture was kept at 20°–25° by external cooling by means of a ice-water bath during the whole addition, then it was kept at this value during 48 hours while stirring.

The mixture was then poured onto crushed ice and, after decantation the organic phase was washed three times with 10 % aqueous solution of sodium bicarbonate. After the usual treatments of drying over anhydrous $Na_2SO_4$ and evaporation of the volatile portions, 14.7 g of an oily raw material were obtained which upon fractional distillation gave 11.9 g (yield 72 %) of the desired lactone.

| | |
|---|---|
| B.p. 92°/0.08 Torr ; | $n_D^{20} = 1.5053$; $d^{20} = 1.136$. |
| IR : | 3450, 2940, 2860, 1820, 1730, 1640, 1470–1455, 1415, 1370, 1321, 1275, 1238, 1199, 1142, 1099, 1058, 1025 cm$^{-1}$; |
| NMR (CDCl$_3$) 90 MHz : | complex absorption at 0.8–2 (13H); 4.5 (1H, m) δ ppm; |
| MS : | M$^+$ = 166 (16); m/e: 67 (100), 41 (88), 80 (84), 95 (70), 39 (69), 93 (67), 79 (63), 68 (61), 81 (59), 98 (58), 122 (57), 97 (57), 69 (41), 27 (40), 123 (30), 55 (30), 42 (30), 53 (29), 109 (25), 138 (8); |
| UV (C$_2$H$_5$OH) : | 203 and 220 nm (ε ca. 60). |

EXAMPLE 2

8-Oxatricyclo[5.3.1.0$^{2,6}$]undec-3-en-9-one and/or 8-oxatricyclo [5.3.1.0$^{2,6}$]undec-4-en-9-one A mixture containing 12 g (0.078 M) of a 50 % solution of peracetic acid in acetic acid containing 0.5 g of anhydrous sodium acetate was added dropwise and under vigorous stirring within 40 minutes to a mixture of 10 g (0.068 M) of tricyclo [5.2.1.0$^{2,6}$]dec-3- and/or -4-en-8-one — available from Ruhrchemie, Bruchstrasse, D-42 Oberhausen-Holten, West Germany — and 6 g of anhydrous sodium acetate in 24 g of dichloromethane.

During the whole addition the temperature of the reaction mixture was kept at 20°–25° by external cooling. 20 ml of dichloromethane were then added and the whole was kept under stirring during 20 hours, whereupon it was poured into a ice-water mixture. The separated organic phase was washed with a 10 % aqueous solution of sodium bicarbonate until neutrality, then it was subjected to the usual treatments of drying and evaporation to give 9 g of a raw material which on distillation yielded 5.9 g of a product showing the following analytical data.

| | |
|---|---|
| B.p. 116°/0.06 Torr ; | $n_D^{20} = 1.5219$; $d^{20} = 1.174$ |
| IR (neat liquid) : | 3020, 2910, 1730, 1620, 1240, 1190, 1062, 1010, 980, 958, 806, 700 cm$^{-1}$; |
| NMR (CCl$_4$) 60 MHz : | 5.5 (2H, m); 4.4 (1H, m); 1.6–3.5 (9H, complex band) δppm |
| MS : | M$^+$ = 164 (46); m/e: 66 (100), 105 (45), 39 (41), 67 (39), 92 (31), 91 (30), 41 (60), 93 (29), 79 (78), 77 (26), 105 (18), 27 (18). |
| UV (C$_2$H$_5$OH) : | λ = 209 nm |

EXAMPLE 3

Fragrance composition

Owing to the specific organoleptic properties shown by 8-oxatricyclo[5.3.1.0$^{2,6}$]undecan-9-one, this compound was used in a proportion of 70 % by weight for the reconstitution of a floral essential oil of liatris in admixture with a composition obtained by mixing together the following ingredients (parts by weight):

| | |
|---|---|
| Dihydrocoumarin | 80 |
| Coumarin | 40 |
| Tolu resinoide at 50 %* | 30 |
| Heliotropin | 30 |
| Isocamphyl-cyclohexanol | 40 |
| Colorless oak moss absolute 50 %* | 30 |
| Flouve essential oil | 20 |
| Lentisque absolute | 20 |
| Ethylvanillin 10 %* | 10 |
| Total | 300 |

*in diethylphthalate

The thus reconstituted composition showed a well defined natural character.

EXAMPLE 4

A base perfuming composition of the type "Fruits d'Automne" was prepared by mixing together the following ingredients (parts by weight):

| | |
|---|---|
| Phenyl-ethyl alcohol | 350 |
| 2,6,6-Trimethyl-1-[but-2-en-1-oyl]-cyclohex-2-ene 10 %* | 200 |
| Cedar oil | 150 |
| Benzyl acetate | 100 |
| Litsea Cubeba oil | 60 |
| Allyl phenoxyacetate | 60 |
| l-Citronellol | 40 |
| Tuberose oil | 40 |
| Total | 1000 |

*in diethyl phthalate

By adding to 950 g of the above composition 50 g of 8-oxatricyclo[5.2.1.0$^{2,6}$]undecan-9-one, there was obtained a novel composition which possessed a more balanced top note and a better harmony when compared with the base composition. This novel composition presented moreover a more marked fruity note together with an original spicy character.

EXAMPLE 5

Aromatization of foodstuffs

Two flavouring base compositions of the buttery walnut type were prepared by mixing together the following ingredients (parts by weight):

| | A (control) | B (test) |
|---|---|---|
| methyl-cyclopentenolone | 50 | 50 |
| furfurol | 50 | 50 |
| furfural | 10 | 10 |
| diacetyl | 5 | 5 |
| acetyl-methylcarbinol | 30 | 30 |
| benzyl alcohol | 100 | 100 |
| propylene glycol | 755 | 605 |
| 8-oxatricyclo[5.3.1.0$^{2,6}$]undecan-9-one | — | 150 |
| Total | 1000 | 1000 |

The test composition possessed when compared with the control composition a better defined caramel like character. It presented moreover a fattier, sweeter and more woody lactonic note. These flavouring characters resemble, at least in part, to those obtained by the utilization of coumarin without, however, showing the flowery character of this latter.

The above given compositions were then used for the aromatization of the following foodstuffs in the given proportions.

1. Sugared milk: A base foodstuff was prepared by dissolving 4 g of commercial sugar into 100 ml of milk.
2. Ice cream: A base foodstuff was prepared by adding 1 liter of pre-heated milk to a mixture comprising 5 egg yolks and 250 g of sugar and the obtained mixture was mixed until a homogeneous cream was obtained. After having been left at water-bath temperature, the mixture hardened and it was allowed then to cool.
3. Cake: The following ingredients were mixed together: 100 g of vegetable margarine, 1.5 g of NaCl, 100 g of sucrose, 2 eggs and 100 g of flour. The flavour was added and the mass was cooked for 40 minutes at 180°.
4. Pudding: To 500 ml of warm milk there was added a mixture of 60 g of sucrose and 3 g of pectin. The mixture was boiled for a few seconds, and the flavour was added. The mixture was then allowed to cool.
5. Chocolate: A commercial chocolate paste of bland taste was warmed to 44° and subsequently tapped by cooling it to 18°–20°, then it was tempered by slowly warming it to 32°–33°. The flavour was added to this paste which was eventually mould filled and left to cool.

| Proportions of flavour in the foodstuffs | |
|---|---|
| 1. Sugared milk | 10 g for 100 l foodstuff |
| 2. Ice-cream | 10 – 15 g for 100 l foodstuff |
| 3. Cake | 20 g for 100 kg foodstuff |
| 4. Pudding | 10 – 15 g for 100 kg foodstuff |
| 5. Chocolate | 25 g for 100 kg foodstuff |

Samples of the finished foodstuffs were tested by a panel of experienced tasters, who all thought that the "test" samples had a more defined caramel taste and possessed, moreover, a pleasant lactonic note.

What is claimed is:
1. A tricyclic lactone of formula

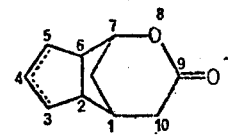

I wherein one of the rings contains a single or a double bond in one of the positions indicated by the dotted lines.

2. 8-Oxatricyclo[5.3.1.0$^{2,6}$]undecan-9-one.
3. 8-Oxatricyclo[5.3.1.0$^{2,6}$]undec-3-en-9-one.
4. 8-Oxatricyclo[5.3.1.0$^{2,6}$]undec-4-en-9-one.

* * * * *

UNITED STATES PATENT AND TRADEMARK OFFICE
CERTIFICATE OF CORRECTION

PATENT NO. : 3,981,892
DATED : September 21, 1976
INVENTOR(S) : Werner Skorianetz It is certified that error appears in the above-identified patent and that said Letters Patent are hereby corrected as shown below:

Column 4, last line, "$\Lambda = 209$ nm" should be -- $\lambda = 209$ nm --.

Signed and Sealed this

First Day of March 1977

[SEAL]

Attest:

RUTH C. MASON
Attesting Officer

C. MARSHALL DANN
Commissioner of Patents and Trademarks